United States Patent
Srivastava et al.

(10) Patent No.: US 10,839,046 B2
(45) Date of Patent: Nov. 17, 2020

(54) MEDICAL RESEARCH RETRIEVAL ENGINE

(75) Inventors: Gitika Srivastava, Cambridge, MA (US); Naresh Ramarajan, Tujunga, CA (US)

(73) Assignee: Navya Network, Inc., Cambridge, MA (US)

( * ) Notice: Subject to any disclaimer, the term of this patent is extended or adjusted under 35 U.S.C. 154(b) by 896 days.

(21) Appl. No.: 13/428,539

(22) Filed: Mar. 23, 2012

(65) Prior Publication Data

US 2013/0254178 A1    Sep. 26, 2013

(51) Int. Cl.
*G06F 19/00* (2018.01)

(52) U.S. Cl.
CPC .................. *G06F 19/324* (2013.01)

(58) Field of Classification Search
CPC .............. G06F 19/324; G16H 70/00
USPC ......... 707/758, 707, 706, 728, 730, 731, 73; 705/2.3, 5.5, 1.5, 10
See application file for complete search history.

(56) References Cited

U.S. PATENT DOCUMENTS

| | | | | |
|---|---|---|---|---|
| 6,049,794 | A | 4/2000 | Jacobs et al. | 706/45 |
| 6,505,196 | B2 * | 1/2003 | Drucker | G06F 17/30699 707/751 |
| 6,581,038 | B1 | 6/2003 | Mahran | 705/3 |
| 6,584,445 | B2 | 6/2003 | Papageorge | 705/3 |
| 7,136,852 | B1 * | 11/2006 | Sterling | G06F 17/30607 |
| 7,213,009 | B2 | 5/2007 | Pestotnik et al. | 706/46 |
| 7,233,912 | B2 * | 6/2007 | Walker | G06Q 10/087 700/231 |
| 7,496,593 | B2 * | 2/2009 | Gardner | G06F 17/279 |
| 7,529,685 | B2 * | 5/2009 | Davies | G06Q 10/10 705/3 |

(Continued)

FOREIGN PATENT DOCUMENTS

| | | | | |
|---|---|---|---|---|
| KR | 10-2009-0072550 | | 7/2009 | ............ G06Q 50/00 |
| WO | 200175728 A1 | | 10/2001 | |

(Continued)

OTHER PUBLICATIONS

LexisNexis Academic and Library Solutions, LexisNexis Academic User Guide, p. 1-35. (Year: 2002).*

(Continued)

*Primary Examiner* — Albert M Phillips, III
(74) *Attorney, Agent, or Firm* — Nutter McClennen & Fish LLP

(57) ABSTRACT

An apparatus and method of retrieving relevant documents having medical research evidence receives a request to access a plurality of documents in a database stored in a memory device. Each of the plurality of documents contains information relating to medical research evidence and has an associated relational expression. The method then causes display of a user interface with a plurality of fields (a set of these fields are selectable, prescribed terms), and receives a relational expression based on information received from the user interface. The received relational expression includes at least one of the selectable, prescribed terms in the user interface. Next, the method compares the received relational expression with the relational expressions associated with at least one of the plurality of documents, and causes the display of information relating to a set of documents in the database as a function of the comparison of relational expressions.

37 Claims, 9 Drawing Sheets

| Show 10V entries | | |
|---|---|---|
| Document No | Grade | View |
| 1 | .8 | ⊖ |
| 2 | 1.1 | ⊖ |

(56) References Cited

U.S. PATENT DOCUMENTS

| | | | |
|---|---|---|---|
| 7,548,917 B2 | 6/2009 | Nelson | 707/7 |
| 7,593,913 B2 | 9/2009 | Wang et al. | 706/62 |
| 7,707,206 B2 | 4/2010 | Encina et al. | |
| 7,769,600 B2 | 8/2010 | Iliff | 705/2 |
| 7,792,884 B2* | 9/2010 | Schlachta-Fairchild | G06F 19/324 707/705 |
| 7,805,385 B2 | 9/2010 | Steck et al. | 706/10 |
| 7,831,444 B2 | 11/2010 | Brown et al. | 705/2 |
| 7,849,400 B2 | 12/2010 | Ritter et al. | 715/234 |
| 7,945,454 B2 | 5/2011 | Firozvi | 705/2 |
| 7,945,497 B2 | 5/2011 | Kenefick et al. | 705/35 |
| 8,024,128 B2 | 9/2011 | Rabinowitz et al. | 702/19 |
| 8,060,531 B2 | 11/2011 | Edelstein et al. | 707/791 |
| 8,095,384 B2 | 1/2012 | Firminger et al. | 705/2 |
| 2003/0088365 A1 | 5/2003 | Becker | 702/19 |
| 2003/0163353 A1 | 8/2003 | Luce et al. | 705/2 |
| 2003/0229513 A1 | 12/2003 | Spertus | 705/2 |
| 2004/0044547 A1* | 3/2004 | Klennert | G06F 19/324 705/2 |
| 2004/0078211 A1* | 4/2004 | Schramm-Apple | G06F 19/324 705/2 |
| 2004/0249664 A1* | 12/2004 | Broverman | G06Q 50/22 705/2 |
| 2004/0260700 A1 | 12/2004 | Wang et al. | 707/10 |
| 2004/0267566 A1 | 12/2004 | Badgett et al. | 705/2 |
| 2005/0256745 A1* | 11/2005 | Dalton | G06Q 10/00 705/3 |
| 2007/0061128 A1 | 3/2007 | Odom et al. | 704/4 |
| 2007/0127597 A1* | 6/2007 | Ammer | G06F 17/30572 375/324 |
| 2007/0173702 A1 | 7/2007 | Dlugos et al. | 600/300 |
| 2008/0172214 A1 | 7/2008 | Col et al. | 703/11 |
| 2008/0195600 A1* | 8/2008 | Deakter | G06F 19/325 |
| 2008/0319942 A1* | 12/2008 | Courdy | G06Q 10/10 |
| 2009/0012842 A1* | 1/2009 | Srinivasan | G06F 16/3344 705/12 |
| 2009/0030945 A1 | 1/2009 | Miller et al. | 707/104.1 |
| 2009/0043733 A1 | 2/2009 | Kingsford et al. | 707/3 |
| 2009/0083075 A1 | 3/2009 | Henschke et al. | 705/3 |
| 2009/0119330 A1 | 5/2009 | Sampath et al. | 707/102 |
| 2009/0144092 A1 | 6/2009 | Vardy | 705/3 |
| 2009/0164237 A1 | 6/2009 | Hunt et al. | 705/2 |
| 2009/0177493 A1 | 7/2009 | Narayan | 705/3 |
| 2009/0177920 A1 | 7/2009 | Richards et al. | 714/15 |
| 2009/0216807 A1* | 8/2009 | Roberts | G16H 15/00 |
| 2009/0299766 A1 | 12/2009 | Friedlander et al. | 705/2 |
| 2009/0313243 A1* | 12/2009 | Buitelaar | G06F 17/30734 |
| 2010/0138199 A1 | 6/2010 | Soto et al. | 703/2 |
| 2010/0145720 A1 | 6/2010 | Reiner | 705/2 |
| 2010/0179831 A1 | 7/2010 | Brown et al. | 705/3 |
| 2010/0191071 A1 | 7/2010 | Anderson et al. | 600/301 |
| 2010/0205006 A1* | 8/2010 | Bergh | 705/3 |
| 2010/0205141 A1* | 8/2010 | Meesa | G16H 10/60 707/602 |
| 2010/0217736 A1 | 8/2010 | Sarel | 706/47 |
| 2010/0217738 A1 | 8/2010 | Sarel | 706/47 |
| 2010/0241454 A1* | 9/2010 | Firminger | G06F 19/3481 705/3 |
| 2010/0241595 A1 | 9/2010 | Felsher | 705/400 |
| 2010/0287213 A1 | 11/2010 | Rolls et al. | 707/803 |
| 2010/0306183 A1* | 12/2010 | Laconi | G06F 19/00 707/706 |
| 2011/0093288 A1 | 4/2011 | Soto et al. | 705/2 |
| 2011/0112860 A1* | 5/2011 | Kehr | G06F 19/3456 705/2 |
| 2011/0238711 A1* | 9/2011 | Schmeink | G06F 16/22 707/807 |
| 2011/0246236 A1* | 10/2011 | Green, III | G06Q 10/06 705/3 |
| 2011/0288890 A1* | 11/2011 | Dalton | G06Q 50/22 705/3 |
| 2012/0016206 A1 | 1/2012 | Ramarajan et al. | |
| 2012/0239420 A1 | 9/2012 | Stapelfeldt et al. | 705/2 |
| 2012/0317136 A1* | 12/2012 | Papish | G06F 17/30035 707/769 |
| 2013/0066648 A1 | 3/2013 | Lipscher et al. | 705/2 |
| 2013/0080470 A1 | 3/2013 | Stergiou et al. | 707/780 |

FOREIGN PATENT DOCUMENTS

| | | | |
|---|---|---|---|
| WO | WO 01/75728 | 10/2001 | G06F 17/60 |
| WO | 200198866 A2 | 12/2001 | |
| WO | WO 01/98866 | 12/2001 | |
| WO | 2003021511 A1 | 3/2003 | |
| WO | WO 03/21511 | 3/2003 | G06F 17/60 |
| WO | 2005034001 A1 | 4/2005 | |
| WO | WO 05/34001 | 4/2005 | G06F 19/00 |
| WO | WO 2009/103156 A1 | 8/2009 | G06F 19/00 |

OTHER PUBLICATIONS

Commissioner of the Korean Intellectual Property Office, International Search Report and Written Opinion for PCT/US2013/033237, dated Jun. 28, 2013, 10 pages.

Office Action issued in Canadian Patent Application No. 2,906,297 dated Oct. 16, 2018 (9 pages).

Patel et al. "Trial X: Using Semantic Technologies to Match Patients to Relevant Clinical Trials Based on Their Personal Health Records", Web Semantics: Science, Services and Agents on the World Wide Web, Elsevier, Amsterdam, NL, vol. 8, No. 4, Nov. 1, 2010, pp. 342-347.

Samson et al. "A Practical Method for Transforming Free-Text Eligibility Criteria Into Computable Criteria", Journal of Biomedical Informatics, vol. 44, No. 02, Apr. 2011, pp. 239-250.

* cited by examiner

Document Input Form

1. Biography

2. Demographics/Table 1

3. Types

4. Prior Treatments

5. Treatments

Cancel

*FIG. 4B*

Bibliography

Paper ID _____

Trial Name _____

Title _____

Authors _____

Journal _____

Demographics/Table 1

| | Median | Lower | Upper | PTC | Count |
|---|---|---|---|---|---|
| Age | ☐ | ☐ | ☐ | ☐ | ☐ |
| Gender | ☐M | ☐F | | ☐Transvestile | ☐Unknown |

| | | PTC | Count |
|---|---|---|---|
| Race | ☐ | | |
| Tumor Size | ☐ | PTC | Count |
| Tumor Grade | ☐ | PTC | Count |
| Histology | ☐ | | |

Include/Exclude

Types

Age:  Lower [ ]     Upper [ ]

Criteria 1 score

- [ ] 100% - normal
- [ ] 90% - capable of . . .
- [ ] 80% - some difficulty
- ...
- [ ] 0% - death

Criteria 2 score

- [ ] 0 - Asymptomatic
- [ ] 1 - mild symptoms
- ...
- [ ] 5 - Death

Criteria N score

- ...

Inclusion

AND [▼]   [ADD]

Exclusion

AND [▼]   [ADD]

*FIG. 4E*

Prior Treatment

Timing  [          ]          Prior treatment  [          ]

Body Part  [          ]

Include/Exclude

*FIG. 4F*

Prior Treatment II

Timing  [          ]          Dosage  [          ]

Prior Treatment  [          ]  Number of
                              Regimens  [          ]
Include/Exclude                Cycles  [          ]

*FIG. 4G*

Treatment

Timing  [          ]          Type of Treatment
                              [          ]

Sample Size
Include/Exclude               [          ]

*FIG. 4H*

MEDICAL RESEARCH RETRIEVAL ENGINE

RELATED APPLICATIONS

This patent application is related to the following co-pending patent applications, the disclosures of which, are incorporated herein, in their entireties, by reference:

U.S. patent application Ser. No. 13/183,757, filed Jul. 15, 2011, and entitled, "Treatment Related Quantitative Decision Engine," which names Naresh Ramarajan and Gitika Srivastava as inventors, and U.S. patent application Ser. No. 13/183,763, filed Jul. 15, 2011, and entitled, "Treatment Decision Engine with Applicability Measure," which names Naresh Ramarajan and Gitika Srivastava as inventors.

FIELD OF THE INVENTION

The invention generally relates to systems and methods for facilitating medical decisions and, more particularly, the invention relates to retrieving medical research documents.

BACKGROUND OF THE INVENTION

Physicians, researchers, and patients often analyze medical literature to learn about the efficacy and results of various patient clinical studies. For example, a physician treating a patient with breast cancer may analyze medical literature to glean best treatment practices used in studies for treating breast cancer patients with similar disease profiles (e.g., stage, type, histology, etc . . . ). Accordingly, to meet those needs, the details of many medical studies often are published as an article in a medical journal, such as the widely known New England Journal of Medicine, and available to the public from any of a number of publicly available and private data stores (e.g., Ovid, Embase, Cinahl, Medline or Pubmed).

While general access to these documents may not necessarily pose a problem, access to the more relevant of these documents does pose a problem—it can be time consuming and yield less relevant documents. Specifically, some commercial databases index medical literature to return publications having exact keywords entered into a search engine. For example, a commercial database may have a search field for entering any search term desired by a researcher. Those databases thus return any article with those terms.

Undesirably, this prior art search process typically returns too many irrelevant documents that must be reviewed in detail. Even more problematic, the search results often omit important articles if the researcher does not enter search terms that are broad enough, or properly targeted, to capture the desired literature.

SUMMARY OF THE INVENTION

In accordance with one embodiment of the invention, an apparatus and method of retrieving relevant documents having medical research evidence receives a request to access a plurality of documents in a database stored in a memory device. Each of the plurality of documents contains information relating to medical research evidence and has an associated relational expression. The method then causes display of a user interface with a plurality of fields (a set of these fields are selectable, prescribed terms), and receives a relational expression based on information received from the user interface. The received relational expression includes at least one of the selectable, prescribed terms in the user interface. Next, the method compares the received relational expression with the relational expressions associated with at least one of the plurality of documents, and causes the display of information relating to a set of documents in the database as a function of the comparison of relational expressions.

Each document may have a different relational expression, or at least two documents may have the same relational expression. In some embodiments, the method compares the received relational expression with the relational expressions associated with more than one of the plurality of documents, or with those of each of the plurality of documents in the database.

The method may cause a display device to display the user interface, and the user interface may have at least one of a plurality of drop-down menus and selectable boxes. Among other ways, a local client may display the user interface, where the database (e.g., having a tangible computer readable medium) communicates with the local client across a public network. For example, the method may enter data into the user interface, and forward the request (to access a plurality of documents) toward the database. The relational expression that drives this process may be derived by any of a number of techniques. For example, the relational expression may include Boolean operators, arithmetic operators (e.g., "<" and ">"), numerical ranges, equations, functions, permutations, and IF/THEN statements.

After the comparison, the method may cause the display of a listing of one or more of the documents. For example, the listing may have at least two documents, and list those documents in order of relevance as a function of the comparison of relational expressions. The listing also may have relevance indicia indicating the relevance of each document in the list as a function of the comparison of the relational expressions. For example, such indicia may include one or more of a percentage and a color.

A given document may have a given relational expression with at least one term that is not present in the given document (and vice versa). The given document accordingly may have a specific term related to, but less broad than, or more broad than, the at least one term in in the relational expression. For example, a document may have the term "any invasive carcinoma" while a it may be stored as "IDC," "ILC," etc. (all types of invasive carcinomas) to enhance searches. Moreover, to add relevant information to the database for a given document, some embodiments receive input information (retrieved from a given document) from an input interface having specified terms, form a given relational expression using the input information, and associate the given logical information with the given document.

In various embodiments, a set of the documents in the database relate to medical studies. The relational expression further includes terms relating to at least one or two of a) inclusion criteria defining a medical condition in a study, b) exclusion criteria defining criteria excluding patients from a study, and c) demographic data of patients in a study. For example, the relational expression may include terms having inclusion criteria and exclusion criteria.

In accordance with another embodiment of the invention, an apparatus for retrieving relevant documents having medical research evidence has a request interface configured to receive a request to access a plurality of documents in a database stored in a memory device. Each of the plurality of documents contains information relating to medical research evidence, and each document has an associated relational expression. The apparatus also has a display module operatively coupled with the request interface. The display module causes display of a user interface with a plurality of fields with selectable, prescribed terms.

The apparatus of this embodiment further has expression interface configured to receive a received relational expression based on information received from the user interface, and a comparator operatively coupled with the expression interface and configured to compare the received relational expression with the relational expressions associated with at least one of the plurality of documents. A display module operatively coupled with the comparator is configured to cause display of information relating to a set of documents in the database as a function of the comparison of relational expressions.

Illustrative embodiments of the invention are implemented as a computer program product having a computer usable medium with computer readable program code thereon. The computer readable code may be read and utilized by a computer system in accordance with conventional processes.

BRIEF DESCRIPTION OF THE DRAWINGS

Those skilled in the art should more fully appreciate advantages of various embodiments of the invention from the following "Description of Illustrative Embodiments," discussed with reference to the drawings summarized immediately below.

FIG. 4B schematically shows a simplified view of a second user interface enabling a user to select among different types of data for entry or searching.

FIG. 4C schematically shows a simplified view of a third user interface enabling a user to enter bibliographic information.

FIG. 4D schematically shows a simplified view of a fourth user interface enabling a user to enter demographic data of patients enrolled in a trial.

FIG. 4E schematically shows a simplified view of a fifth user interface enabling a user to enter disease-type data.

FIG. 4F schematically shows a simplified view of a sixth user interface enabling a user to enter prior treatment data.

FIG. 4G schematically shows a simplified view of a seventh user interface enabling a user to enter more specific prior treatment data.

FIG. 4H schematically shows a simplified view of an eighth user interface enabling a user to enter current treatment data tested in the trial.

DESCRIPTION OF ILLUSTRATIVE EMBODIMENTS

Figure 1:
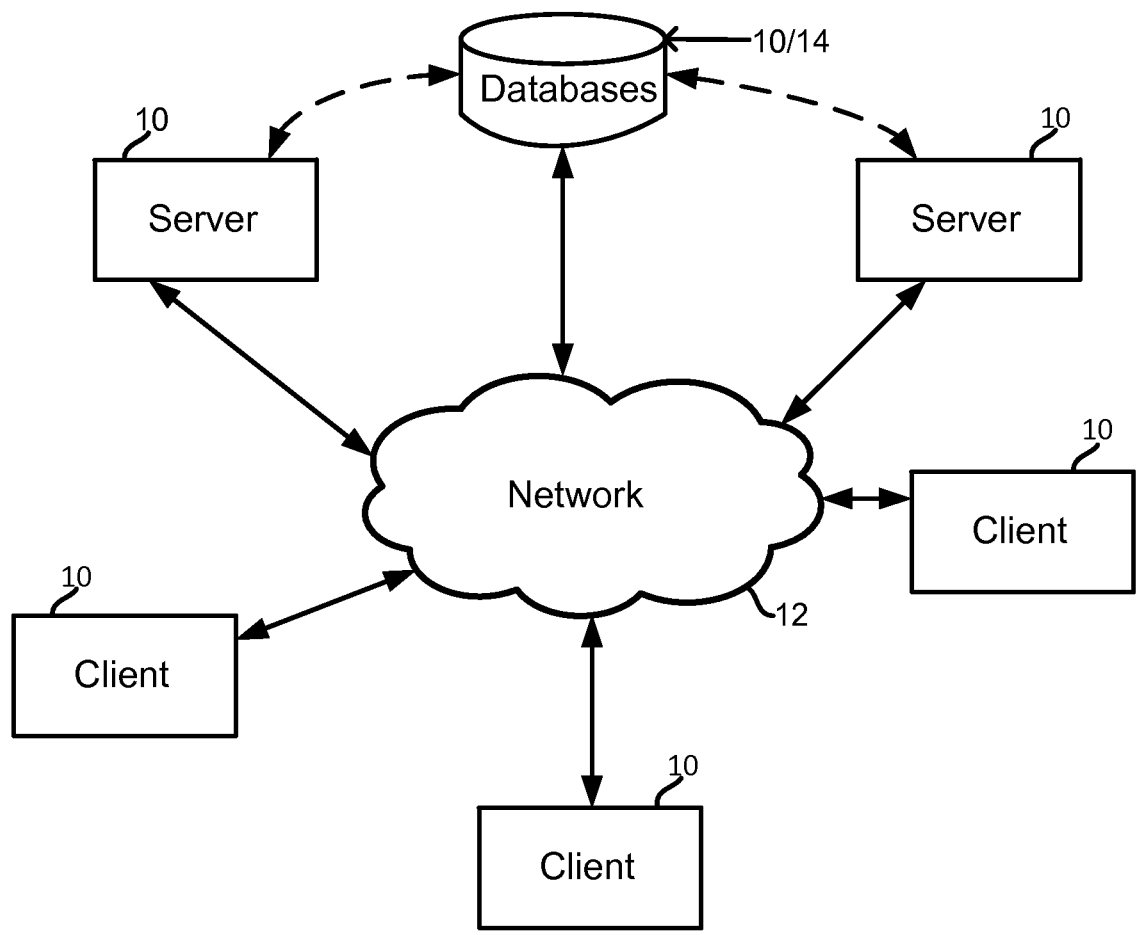
FIG. 1 schematically shows a network that may implement illustrative embodiments of the invention.

In illustrative embodiments, a system for managing documents having medical research evidence is configured to store and retrieve documents in a more precise manner than conventional medical evidence data stores. Consequently, when researching a relevant topic, such as an appropriate treatment for a clinically ill patient, a physician or researcher can retrieve more relevant documents to more efficiently assist in that treatment or research.

More specifically, in illustrative embodiments, the ability to index and search across medical literature is derived from standardized indexing of certain medical research evidence papers using a prescribed medical ontology (or a taxonomy or prescribed selectable items with hierarchical relationships to each other). In some embodiments, the ontology defines hierarchies and logical relationships between categories and sub-categories (often referred to as "fields"), as well as between the values that are possible in a category (often referred to as "validations"). For example, a widely understood ontology is the taxonomy of living species. The classification from Kingdom, Order, Family, Genus and Species with all its implied relationships is an ontology for any living species to be classified. Similarly, some medical ontologies classify different diseases into groups, and relate sub-types of these diseases in a hierarchical manner. Furthermore, this idea can be extended to pathology reports, or radiology reports, among other things, and medical data where the key fields that are unique and comprise the report can be identified and related in a hierarchical and logical manner such that they form a specific ontology.

Though several medical ontologies may exist, various embodiments form an ontology that is not one of the disease as it is derived from the patient's case history. Instead, such embodiments form an ontology of the disease as derived from the medical evidence. This is an important difference. Most medical ontologies are designed for case files/histories of specific patients. However, medical researchers often define fields much more specifically in the research and literature as it calls for more standardization and ability to reproduce results. Thus, an ontology defined from the medical literature, such as those discussed herein, is significantly more specific than ontologies derived from clinical cases. For example, a medical ontology may have a field of Chest Pain with validations of (Typical, Atypical, Non-Cardiac, No Chest Pain, All of the Above). However, an ontology derived from the evidence would be much more specific, defining a field of Chest Pain, with subfields of Duration (hours, days, weeks), Location (substernal, right chest, left chest), Quality, etc. . . . This example is for illustrative purposes only and the specificity is often more than two or three hierarchical levels in order to enhance the reproducibility of the study in question.

Illustrative embodiments form a deductively derived ontology by analyzing the medical literature and creating key fields and validations that make up inclusion criteria, exclusion criteria, and demographic data (each discussed in greater detail below) for the body of research in each disease. This ontology is then systematically mapped back to each individual paper in order to create strings of fields and validations that are linked with Boolean or other operators, thus creating the unique logical expression associated with that research paper. This process allows for more effective and efficient indexing and searching the papers.

The mapping of an ontology designed from the medical evidence back onto individual research articles, and creating logical expressions, enables personalized, case based search. Every patient's case history also may be stored in the same fields and validations of the ontology, and can be expressed as a logical expression as well. Thus, one may have the ability to search from the cases and match the source expression onto the database and the target expression, producing a list of highly specific matches. This eliminates repeated searches, false positives, and false negatives that require extensive manual editing.

In the same way that case based search is enabled, illustrative embodiments also offer broader, novel expression based searches. For example, instead of inputting the details of a specific case, a user of the system can input a created expression that would include multiple validations from the same field, at times expressed as a range or a logical combination therein. For example, the user may search for all papers conducted in patients above the age of 80 (not possible in the case based search as a patient cannot be both age 85 and age 90). These broader searches have utility to researchers, physicians, and students learning about the research present on a disease and the demographics studied in the literature.

Accordingly, the combination of unique ontological mapping of research articles and patient cases, storing them as logical expressions, and matching source and target expressions to generate a very specific search result facilitates more effective search. Various embodiments achieve patient specificity by carefully selecting the fields in the article from which the ontology and logical expressions are derived. These are, specifically, patient eligibility criteria for the study (inclusion and exclusion criteria) and the demographic data of patients that were actually analyzed in the article. A patient's case file data is matched with the ranges and logical combinations of the eligibility criteria and the demographic data to create the patient specific search result. Some embodiments also have the ability to index and search by the combination of the eligibility criteria and treatment tested in the article and by bibliography, as well as common meta-tagged keywords on the paper such as the MeSH terms from Medline (Medical Subject Headings). Details of illustrative embodiments are discussed below.

FIG. 1 schematically shows a portion of a network that may be used with illustrative embodiments of the invention. To that end, the network has a plurality of computer devices 10 in, about, and interconnected by a public or private network 12, which is represented by a cloud and referred to herein as "the cloud." For example, the cloud may include the Internet or a virtual private network (VPN). Moreover, each of the computer devices 10 in the network may be part of another network, such as a local area network or wide area network, while two or more of the computer devices 10 shown may be part of the same smaller sub-network.

The computer devices 10 generically are represented as clients requesting services, servers delivering services, and databases storing medical research documentary data. Databases storing medical research documentary data (also referred to herein as "medical research evidence") are identified by reference number 14. Among other things, the computer devices 10 may include typical multipurpose computers (e.g., desktops, laptops, etc . . . ), tablets, e-readers, smartphones, mobile telephones, SMS services, mobile Internet devices, or other conventional computer devices capable of communicating and operating in the manner described herein. The servers thus may have much of the functionality described below, such as the process of managing data storage and retrieval within the databases 14. Some of that logic, however, may be distributed among various servers, clients, and/or other devices not shown. Accordingly, discussion of functionality on a single device is but one of many anticipated implementations.

If the cloud is the Internet, for example, a client may access a server providing the noted services through a graphical user interface presented on a webpage displayed by the client computer. The relevant client and server thus may communicate by forwarding messages toward each other across the cloud (or within their smaller sub-network, if that is the case), and receiving those messages, in an effort to appropriately accomplish the desired function.

Figure 2:
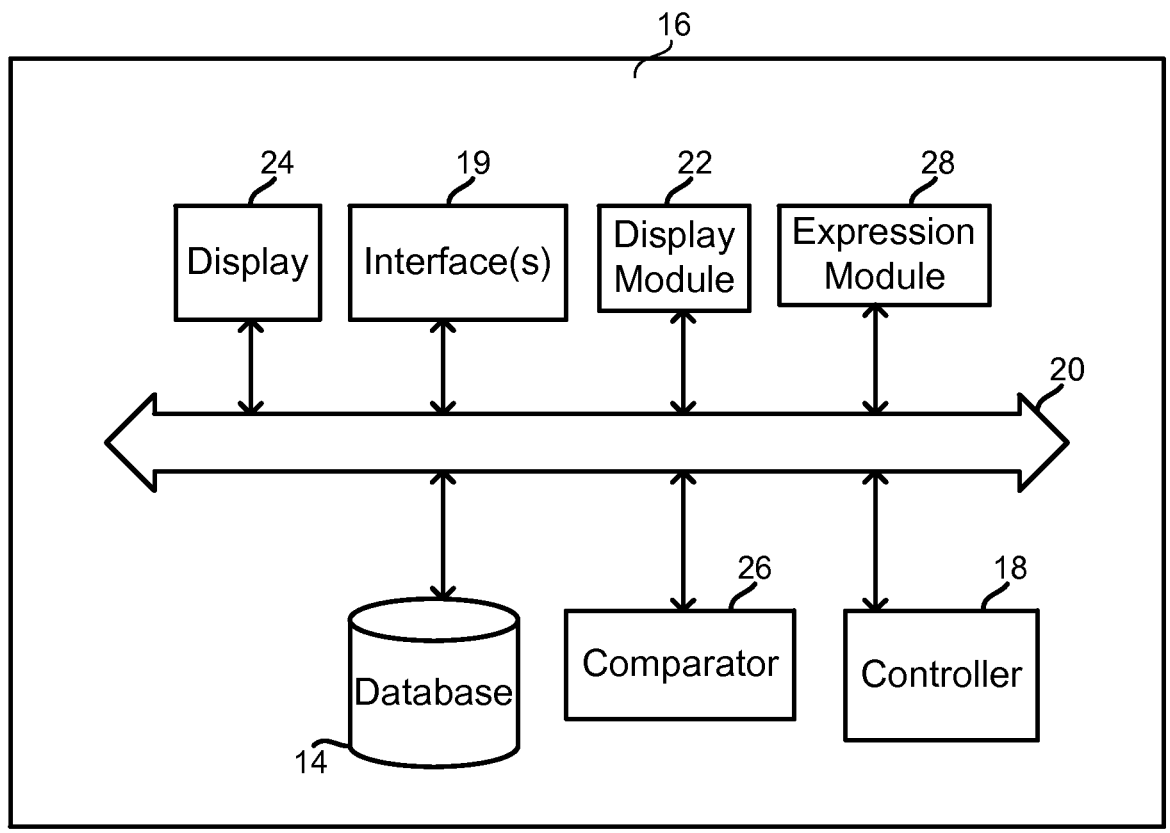
FIG. 2 schematically shows an apparatus configured in accordance with illustrative embodiments of the invention for storing and retrieving documents having medical research evidence.

FIG. 2 schematically shows a document management engine 16 configured in accordance with illustrative embodiments of the invention for storing and retrieving documents having medical research evidence. This engine 16, which may include either or both hardware and software, can provide much of the functionality described herein. For example, the document management engine 16 can control communication between a server and a client to appropriately index and store documents in the database 14, manage graphical user interfaces for document storage and retrieval, form and assign relational expressions to documents for subsequent retrieval, and manage searching operations of the requisite databases 14.

A relational expression may be an expression of a single datum, or a combination of data related by one or more relationships. For example, the relational expression may include Boolean operators, arithmetic operators (e.g., "<" and ">"), numerical ranges, equations, functions, permutations, and IF/THEN statements. Thus, a logical expression may be a type of relational expression. For simplicity, much of the below discussion relates to logical expressions. Those in the art should understand, however, that various embodiments are not limited to logical expressions and apply more broadly to other relational expressions.

The document management engine 16 has a controller 18 for managing performance of the engine 16 across a common bus 20. In other words, the controller 18, which can have its functionality spread among various of the different modules in the engine 16, directs the overall performance and some specific processes of the document engine 16. Among other things, the controller 18 manages an interface 19 that forwards and receives messages to and from other computing devices across the network 12. For example, the interface 19 may forward a message to a client, across the cloud, having a listing of documents retrieved from a local database 14. The database 14 also is shown as being in communication with the common bus 20. Although a single interface 19 is shown, those skilled in the art can use a plurality of different interfaces, depending upon the implementation. Accordingly, discussion of a single interface 19 is for illustrative purposes only.

The document engine 16 has a number of other functional modules, such as a display module 22 that causes the display of certain information on a display device 24 that optionally may be included with the document engine 16, and an expression module 28 for formulating logical expressions to be associated with certain documents. In addition, the document engine 16 also has a comparator 26 for generating a list of relevant documents based on the logical expressions associated with the documents in the database 14.

It should be noted that the common bus 20 is merely one potential manner for the modules to communicate. The document engine 16 may have any of a number of different communication schemes for inter-module communication, such as serial communication, or a combination of parallel and serial communications. Accordingly, discussion of the bus 20 is for illustrative purposes only. Moreover, like the controller 18, the functionality of the various modules shown in FIG. 2 can be consolidated into a single modules, or spread among various other modules, such as the modules shown and other modules that are not shown. Further functional modules may be added to optimize performance.

In some embodiments, the document engine 16 omits some of the noted modules, such as the display or database 14, which then may be physically separated from the other modules by a wire and/or intervening network. For example, the database 14 shown in the document engine 16 of FIG. 2 can be:

1) the same database, on a separate computer device, shown in FIG. 1, or 2) a portion of a distributed database that includes the database 14 of FIG. 1.

Accordingly, use of the term "module," description of the modules arranged in the manner shown in FIG. 2, and discussion of the entire document engine 16 should not limit various embodiments.

Figure 3:
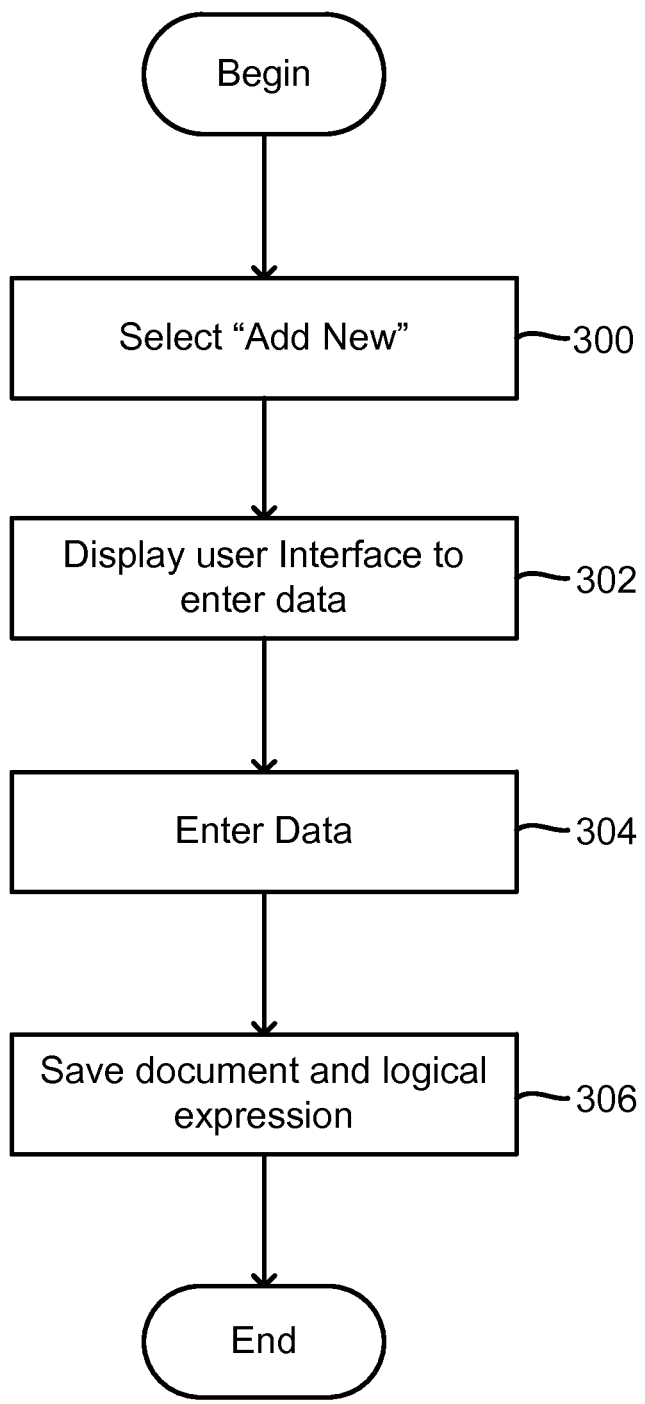
FIG. 3 shows a process of adding new documents to the medical document database of FIGS. 1 and 2.

FIG. 3 shows a process of adding new documents to the medical document database 14 of FIGS. 1 and 2. It should be noted that in much of this discussion, the medical research evidence/documents relate to a specific illness—namely, breast cancer in this example. That discussion of breast cancer is merely illustrative, however, and not intended to limit various embodiments of the invention. Accordingly, those skilled in the art can apply principles of various embodiments to other medical research topics and illnesses.

Figure 4A:
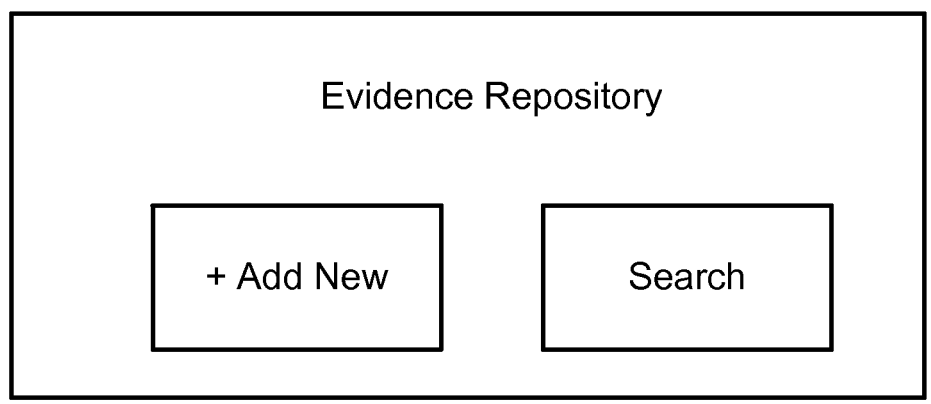
FIG. 4A schematically shows a simplified view of a first user interface enabling a user or to either add a new document to the database, or search documents in the database.

A user may initiate the process by displaying a graphical user interface on their local display device. FIG. 4A schematically shows one such graphical user interface, which includes an "add new" button for enabling the user to add new documents to the database 14, and a "search" button for enabling the user to search through the documents in the database 14.

The process of adding new documents to the database 14 thus begins at step 300, in which the user selects the "add new" button of FIG. 4A. The system responsively displays a second user interface for entering specific data (step 302). FIG. 4B schematically shows an example of one such second user interface for a database 14 directed toward breast cancer evidence. In that example, a user or an automated process enters data, from the paper itself, in five different categories for a single paper/document. Those five different categories are as follows:

1) Biography: biographical information, such as the trial name, title, authors, journal title, year of publication, volume number, etc. . . .
2) Demographics (also known as "Table 1" information from certain publications, such as those from the New England Journal of Medicine): demographics of people actually in the study, such as number of people of certain ages, genders, races, Karnofsky scores, etc. . . .
3) Types: specific type of illness analyzed by the study, e.g., the information to identify the specific type of breast cancer. For example, this could list Karnofsky score, ECOG score, how the diagnosis was made, menopausal status, etc. . . .
4) Prior Treatments: treatments for the specific illness or a different illness. For example, breast surgery, lymph node surgery, radiation, biopsy, etc. . . .
5) Treatments: current treatments for the specific illness or for a different illness. For example, breast surgery, lymph node surgery, radiation, biopsy, etc. . . .

Next, the process continues to step 304, in which the user or automated process enters document specific data into the database 14. FIGS. 4C-4H schematically show a number of different graphical user interfaces that enable the user to enter the data. As discussed above and below, the graphical user interfaces permit only specific terms to be stored. Each user graphical user interface is discussed immediately below.

FIG. 4C schematically shows a graphical user interface for entering biographical information. As noted above, this information includes a number of different fields. FIG. 4C only shows a few of many different fields. Those in FIG. 4C include:
Paper identification number
Trial name
Paper Title
Authors
Journal FIG. 4D schematically shows a graphical user interface for entering demographic information relating to the pool of people (or animals, as the case may be) in the study. This data may include:
Age
Gender
Race
Tumor Size
Histology As shown, the fields of the graphical user interface of FIG. 4D are considered to be "closed" because the user can only enter data from a menu of specific, prescribed selections. For example, in the Gender field, the user can only select the "M," "F," "transvestite" or "unknown" checkboxes. The user cannot enter different data. In other words, when entering data into a field, the user can only select from a set of one or more prescribed terms. These prescribed terms can be in any convenient form, such as checkboxes, or in a drop down menu (among others).

This closed format requires a user to make certain decisions when entering the data. For example, assume that the document is related to some specific criteria or species of information, such as a beagle (i.e., a type of dog), but never discusses dogs in general. In fact, the document may not even use the terms "canine," "dog," or the like. Also assume that one of two prescribed terms for a given field is "dog," while another is cat. The user or machine entering the data in the database 14 recognizes that a beagle is a type of dog, and would select "dog" from the list. Accordingly, the data entered into the database 14 may be broader in scope than those in the document. In addition, data entered into the database 14 for a given document may not even be the same term used in the document.

In alternative embodiments, some fields can be closed as described above, while other fields permit the user to enter any data. The latter type of fields thus may be considered to be "open" fields.

FIG. 4E schematically shows another graphical user interface for entering "Type" information. This data may include:
Age (open field).
Different criteria for identifying the disease. This criteria may be any of a number of items, such as, for breast cancer, Karnofsky score, ECOG score, etc. . . .

The open field of age (or other field) may be somewhat limited. For example, the graphical user interface can automatically round the number to the next highest number. Alternatively, the open field may simply enter the data as entered.

The graphical user interface of FIG. 4E also has an expression area for forming a logical expression associated with the document. More specifically, as noted above, during the data entry process, the above noted expression module 28 forms and associates a logical expression for each document. These logical expressions are used to identify and, during a later process, retrieve the most relevant documents. To that end, the expression area in FIG. 4E has an "inclusion" area defining medical conditions, patient criteria (e.g., age, gender), and/or treatments (e.g., radiation therapy, chemotherapy) of patients deemed to be acceptable by a study in the document. In addition, the expression area also has an "exclusion" area defining medical conditions, patient criteria and/or treatments of patients excluded from the same study.

In the embodiment shown, the inclusion and exclusion areas each have a drop down menu of Boolean operators (e.g., AND and OR), and an "add" button to add data to the respective areas. The expression module 28 and/or user thus can select specific criteria to add in a specialized manner to the inclusion or exclusion areas. It should be noted that other types of logical expressions should suffice. Accordingly, discussion of Boolean expressions is but one exemplary logical expression type anticipated by various embodiments.

Below is an example of a summary of a specific document and how its logical expression is developed in one embodiment:

EXAMPLE 1

Enrollment required a confirmed diagnosis of breast cancer with HER2 protein positivity (either IHC 3+ or FISH overexpressed). Women with node positive disease as well as high risk node negative disease (defined as node negative disease where the tumor is more than 2 cm and positive for estrogen receptor or progesterone receptor, or tumor more than 1 cm and negative for estrogen receptor and progesterone receptors) were eligible. Other requirements were adequate bone marrow, liver, and kidney function and heart function that was normal. Patients with evidence of distant disease spread (metastasis) were excluded. Surgical removal of the tumor and lymph nodes was required. Patients were ineligible if they had a history of heart attacks or heart disease.

INCLUSION:
1. Breast Cancer AND
2. HER2 protein positivity (IHC 3+ OR FISH overexpressed) AND
3. (Node positive Disease OR
4. Node Negative AND (((tumor >2 cm AND (estrogen receptor positive OR progesterone receptor positive)) OR (tumor >1 cm AND estrogen receptor negative AND progesterone receptor negative)) AND
5. adequate bone marrow function AND
6. adequate Liver function AND
7. adequate kidney function AND
8. Normal Cardiac function AND
9. Surgical removal of tumor AND
10. Surgical removal of lymph nodes
EXCLUSION (as from paragraph):
1. Distant disease spread (metastasis) AND
2. History of heart attacks AND
3. History of heart disease This can be more specifically translated into the following expression:
INCLUSION:
1. Clinical Diagnosis: Operable Breast Cancer AND
2. HER2 Receptor: (IHC 3+ OR FISH overexpressed) AND
3. (Axillary Pathological Lymph Node: yes OR
4. Axillary Pathological Lymph Node: no AND ((Pathological tumor size lower limit 2 cm AND (Estrogen Receptor: positive OR Progesterone Receptor: positive)) OR (Pathological tumor size lower limit 1 cm AND Estrogen receptor: negative AND progesterone receptor negative)). AND
5. Bone marrow (Hematologic) function: adequate AND
6. Liver (Hepatic) function: adequate AND
7. Kidney (Renal) function: adequate AND
8. Heart (Cardiac) function: adequate AND
9. Prior Treatment Surgery: Primary surgery AND
10. Prior Treatment Lymph Node: (SLND OR ALND)
EXCLUSION:
1. Metastasis: yes AND
2. Other past medical history: History of heart disease FIGS. 4F and 4G schematically show two graphical user interfaces for entering data about prior treatments. Both graphical user interfaces have different selection criteria since they relate to different prior treatments. Specifically, the prior treatment of FIG. 4F has dropdown menus of Timing and Body Part, while the prior treatment of FIG. 4G also has Timing, but, rather than have Body Part, has Number of Regimens, and Cycles. These two graphical user interfaces demonstrate how different treatments often have different specific issues and methods of treatment and thus, they may have different interfaces. In addition, one or both of these graphical user interfaces may have a button to determine inclusion and exclusion criteria.

FIG. 4H schematically shows yet another graphical user interface for a current treatment of subjects in the study (or studies). In a manner similar to the graphical user interfaces of FIGS. 4F and 4G, this treatment graphical user interface includes its own specific drop down menus/fields for the specific type of treatment, and a button to determine inclusion and exclusion criteria.

It should be noted that the graphical user interfaces are not necessary if an automated process enters the data. In that case, the automated process cooperates with the engine 16 to enter the data with the prescribed terms in a manner similar to the process discussed herein.

Returning to FIG. 3, after entering the data at step 304, the process continues to step 306 by saving 1) the document or a document identifier, and 2) the logical expression in the database 14. To that end, the controller 18 first may form the logical expression and validate it (ensure it has no obvious errors), and then store the logical expression as metadata or other data associated with the document. In some embodiments, however, only the metadata and an identifier associated with the document are stored. Thus, if the document is needed, the identifier can help direct the system to the actual location of the document (e.g., an off-site data store, to a web site containing a copy of the document, or a local data store). Among other things, the document identifier can include a pointer to the document itself, or indicia identifying the document.

As shown, the fields and prescribed terms that can be selected typically are highly customized to a specific set of facts. For example, the fields and prescribed terms in the above noted graphical user interfaces relate to breast cancer. Similar principles can apply to other type of medical conditions or medical issues, such as lung cancer, arthritis, flu, pulmonary disease, or heart disease.

This process forms an indexed database 14 that can produce highly relevant evidence/papers/documents for a given query (i.e., the documents themselves, or indicia identifying relevant documents). Each document in the database may have a different logical expression than others in the database, or two or more documents in the same database can share the same logical expression.

Figures 5, 6:
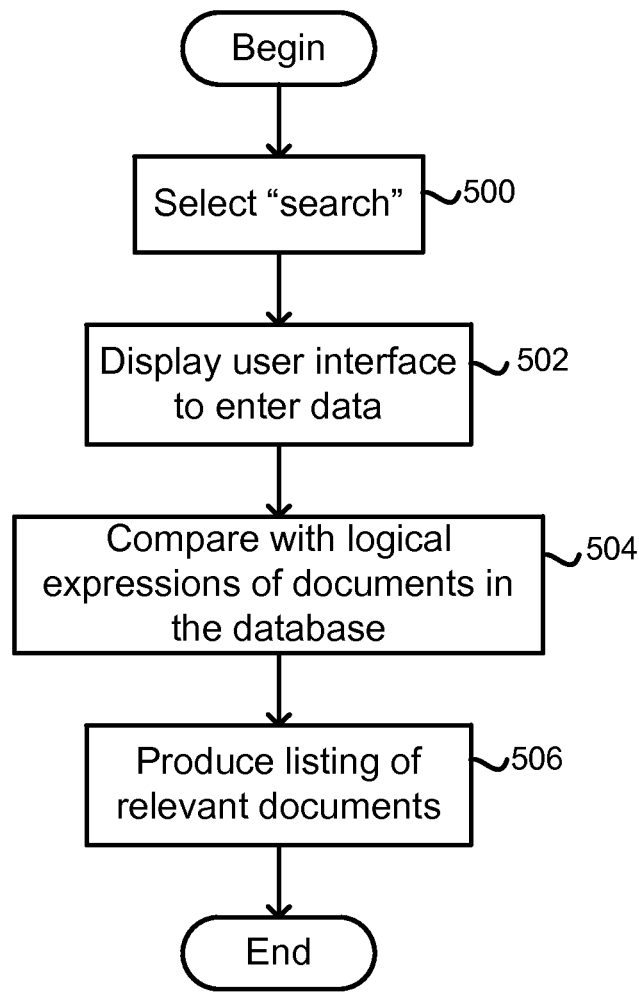
FIG. 5 shows a process of searching for documents having medical research evidence in accordance with illustrative embodiments of the invention.
FIG. 6 schematic a shows a simplified view of a listing of documents retrieved during a document search.

FIG. 5 shows a process of searching for relevant documents in accordance with illustrative embodiments of the invention. The process begins by selecting the "search" button of the graphical user interface shown in FIG. 4A. That causes the display module 22 to cause the user's display device to display a graphical user interface for entering search criteria. In illustrative embodiments, this graphical user interface is either identical to or very similar to those used to enter the data (FIGS. 4B-4H). This gives the user the ability to form logical expressions that ideally are identical to, or very similar to, those associated with the stored documents.

It is anticipated that, for some uses of the document engine 16, the logical expression delineates the exact type of patient the user is treating or researching. For example, if the user is a physician treating a specific type of patient, then that physician should enter data that forms a logical expression that returns all documents in the database 14 with studies that most closely relates to that patient. In this case, among other things, some embodiments may use a form or case based search. See, for example, the co-pending patent applications incorporated above for further information.

Alternative embodiments may have another database containing patient specific medical data. For example, it may include a database of patient specific records in electronic form. These records may have been produced using selectable forms similar to those described above. Creation of these records will cause production of a logical expression that is associated with that record. Subsequently, a single click on a search indicia, such as a search button, can initiate this search process with the medical research evidence database 14.

After forming a logical expression using the graphical user interfaces, the process continues to step 504, in which the comparator 26 compares the logical expression formed by the user with those in the database 14. This comparison is simplified by the fact that both logical expressions have common terms as prescribed in the graphical user interfaces.

The process concludes at step 506 when the display module 22 receives, as a function of the comparison, indicia identifying a set of zero or more relevant documents that the control module considers relevant. The display module 22 then causes display, on some display device, of information relating to that set of documents. The display can be in any convenient form, such as in the form of a list, such as that shown in FIG. 6. In some embodiments, the results can be listed in order of relevance based on the comparison, which can be identified by some relevance indicia, such as a percentage (e.g., 100 percent being an exact match), a position on a listing, or a certain color. Percentages less than 100, for example, may represent partial or incomplete matches. The results in FIG. 6, for example, provide a grade and optional buttons for viewing select documents. See, for example, the co-pending patent applications incorporated above for further information.

In illustrative embodiments, as noted above, this process is carried out across a network, such as the "cloud." For example, the storage and search processes can be delivered in a "software as a service" platform (known as "SAAS") between a server and multiple clients. To that end, the controller 18 sends and receives the relevant messages through one or more of the interfaces 19 in the engine 16 (FIG. 2) as discussed above. In carrying out that process, the display module 22 can generate instructions that, when executed by a client computer, causes the local client computer to display the various graphical user interfaces. In addition, various embodiments can be integrated into the system as described in the two patent applications that were incorporated by reference.

Alternative embodiments, however, may perform the entire process on a local network, such as a local area network, or on or with a single computer system (e.g., a personal computer, a high performance computer, a tablet, a smartphone, or any other similar device) as a stand-alone computer program product. Moreover, some embodiments apply to non-medical research evidence. For example, some embodiments may apply to a branch of science (e.g., research relating to certain bacterium) or a branch of business (e.g., relating to an automobile sales and experiences of new owners).

Various embodiments of the present invention may be embodied in many different forms, including, but in no way limited to, computer program logic for use with a processor (e.g., a microprocessor, micro controller, digital signal processor, or general purpose computer), programmable logic for use with a programmable logic device (e.g., a Field Programmable Gate Array (FPGA) or other PLD), discrete components, integrated circuitry (e.g., an Application Specific Integrated Circuit (ASIC)), or any other means including any combination thereof.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as Fortran, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) in a tangible storage medium, such as a semiconductor memory device (e.g., a RAM, ROM, PROM, EEPROM, or Flash-Programmable memory), a magnetic memory device (e.g., a diskette or fixed disk), an optical memory device (e.g., a CD-ROM), a PC card (e.g., PCMCIA card), or other memory device. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or temporarily in a tangible storage medium, such as a semiconductor memory device (e.g., a RAM, ROM, PROM, EEPROM, or Flash-Programmable memory), a magnetic memory device (e.g., a diskette or fixed disk), an optical memory device (e.g., a CD-ROM), or other memory device. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Additional embodiments of the present invention are listed hereinafter, without limitation. Some embodiments provided for below are described as computer-implemented method claims. However, one of ordinary skill in the art would realize that the method steps may be embodied as computer code and the computer code could be placed on a nontransitory computer readable medium defining a computer program product.

Although the above discussion discloses various exemplary embodiments of the invention, it should be apparent that those skilled in the art can make various modifications that will achieve some of the advantages of the invention without departing from the true scope of the invention.

What is claimed is:

1. A method of retrieving relevant documents having medical research evidence, the method comprising:
   receiving a request to access a plurality of documents in a database stored in at least one memory device, each of the plurality of documents containing information relating to medical research evidence, each document having an associated pre-defined relational expression, wherein the pre-defined relational expression defines a link between fields in a preexisting medical ontological hierarchy that was derived deductively from a plurality of medical literature and separately mapped onto each of the plurality of documents to determine the fields of the pre-defined relational expression;
   causing display of a user interface with a plurality of fields of the preexisting medical ontological hierarchy, a set of the fields having selectable prescribed terms;
   generating a received relational expression based on information received from the user interface, the received relational expression including at least one of the selectable prescribed terms in the user interface;
   comparing the received relational expression with the pre-defined relational expressions associated with at least one of the plurality of documents; and
   causing display of information relating to a set of documents in the database as a function of the comparison of relational expressions.

2. The method as defined by claim 1 wherein each document has a different relational expression.

3. The method as defined by claim 1 wherein at least two documents have the same relational expression.

4. The method as defined by claim 1 wherein comparing comprises comparing the received relational expression with the pre-defined relational expressions associated with more than one of the plurality of documents.

5. The method as defined by claim 1 wherein comparing comprises comparing the received relational expression with the pre-defined relational expressions associated with each of the plurality of documents.

6. The method as defined by claim 1 wherein causing display of a user interface comprises causing a display device to display the user interface.

7. The method as defined by claim 1 wherein the user interface comprises at least one of a plurality of drop-down menus and selectable boxes.

8. The method as defined by claim 1 wherein a local client displays the user interface, the database communicating with the local client across a public network.

9. The method as defined by claim 1 wherein the database comprises a tangible computer readable medium.

10. The method as defined by claim 1 wherein the relational expression comprises Boolean operators.

11. The method as defined by claim 1 further comprising:
    entering data into the user interface; and
    forwarding the request to access a plurality of documents toward the database.

12. The method as defined by claim 1 wherein causing display of information relating to a set of documents comprises causing display of a listing of one or more of the documents.

13. The method as defined by claim 12 wherein the listing comprises at least two documents, the method further comprising listing the documents in order of relevance as a function of the comparison of relational expressions.

14. The method as defined by claim 13 wherein listing comprises including relevance indicia indicating the relevance of each document in the list as a function of the comparison of the relational expressions.

15. The method as defined by claim 14 wherein the indicia includes one or more of a percentage and a color.

16. The method as defined by claim 1 wherein a given document has a given relational expression, the given relational expression including at least one term that is not present in the given document.

17. The method as defined by claim 16 wherein the given document has a specific term related to the at least one term in the given relational expression, the at least one term in the given relational expression being broader than the specific term.

18. The method as defined by claim 1 further comprising:
    receiving input information from an input interface having specified terms, the input information being retrieved from a given document by mapping the preexisting medical ontological hierarchy onto the given document;
    forming a given relational expression using the input information; and
    associating the given relational expression with the given document.

19. The method as defined by claim 1 wherein a set of the documents relate to medical studies, the relational expression including terms relating to at least two of a) inclusion criteria defining a medical condition in a study, b) exclusion criteria defining criteria excluding patients from a study, and c) demographic data of patients in a study.

20. The method as defined by claim 1 wherein the received relational expression comprises a logical expression.

21. An apparatus for retrieving relevant documents having medical research evidence, the apparatus comprising:
    a request interface, executed by a processor on a computer, configured to receive a request to access a plurality of documents in a database stored in a memory device, each of the plurality of documents containing information relating to medical research evidence, each document having an associated pre-defined relational expression, wherein the pre-defined relational expression defines a link between fields in a preexisting medical ontological hierarchy that was derived deductively from a plurality of medical literature and separately mapped onto each of the plurality of documents to determine the fields of the pre-defined relational expression;

a display module, executed by the processor on the computer and operatively coupled with the request interface, the display module causing display of a user interface with a plurality of fields of the medical ontological hierarchy, a set of the fields being selectable prescribed terms;

an expression interface, executed by a server and configured to generate a received relational expression based on information received from the user interface, the received relational expression including at least one of the selectable prescribed terms in the user interface;

a comparator, executed by the server and operatively coupled with the expression interface, the comparator being configured to compare the received relational expression with the pre-defined relational expressions associated with at least one of the plurality of documents; and a display module, executed by the processor on the computer and operatively coupled with the comparator, the display module being configured to cause display of information relating to a set of documents in the database as a function of the comparison of relational expressions.

22. The method as defined by claim 21 wherein the user interface comprises at least one of a plurality of drop-down menus and selectable boxes.

23. The method as defined by claim 21 wherein the relational expression comprises Boolean operators.

24. The method as defined by claim 21 wherein a given document has a given pre-defined relational expression, the given pre-defined relational expression including at least one term that is not present in the given document.

25. A computer program product including a non-transitory computer readable medium having computer code thereon for retrieving relevant documents having medical research evidence, the computer program product comprising:

program code for receiving a request to access a plurality of documents in a database stored in a memory device, each of the plurality of documents containing information relating to medical research evidence, each document having an associated pre-defined relational expression, wherein the pre-defined relational expression defines a link between fields in a preexisting medical ontological hierarchy that was derived deductively from a plurality of medical literature and separately mapped onto each of the plurality of documents to determine the fields of the pre-defined relational expression;

program code for causing display of a user interface with a plurality of fields of the medical ontological hierarchy, a set of the fields being selectable prescribed terms;

program code for generating a received relational expression based on information received from the user interface, the received relational expression including a term related to at least one of the selectable prescribed terms in the user interface;

program code for comparing the received relational expression with the pre-defined relational expressions associated with at least one of the plurality of documents; and program code for causing display of information relating to a set of documents in the database as a function of the comparison of relational expressions.

26. The computer program product as defined by claim 25 wherein at least two documents have the same relational expression.

27. The computer program product as defined by claim 25 wherein the program code for comparing comprises program code for comparing the received relational expression with the pre-defined relational expressions associated with more than one of the plurality of documents.

28. The computer program product as defined by claim 25 wherein the program code for causing display of a user interface comprises program code for causing a display device to display the user interface.

29. The computer program product as defined by claim 25 wherein the user interface comprises at least one of a plurality of drop-down menus and selectable boxes.

30. The computer program product as defined by claim 25 wherein the database comprises a tangible computer readable medium.

31. The computer program product as defined by claim 25 wherein the relational expression comprises Boolean operators.

32. The computer program product as defined by claim 25 wherein the program code for causing display of information relating to a set of documents comprises program code for causing display of a listing of one or more of the documents.

33. The computer program product as defined by claim 32 wherein the listing comprises at least two documents, the computer program product further comprising program code for listing the documents in order of relevance as a function of the comparison of relational expressions.

34. The computer program product as defined by claim 33 wherein the program code for listing comprises program code for including relevance indicia indicating the relevance of each document in the list as a function of the comparison of the relational expressions.

35. The computer program product as defined by claim 34 wherein the given document has a specific term related to the at least one term, the at least one term being broader than the specific term.

36. The computer program product as defined by claim 25 further comprising:

program code for receiving input information from an input interface having specified terms, the input information being retrieved from a given document by mapping the preexisting medical ontological hierarchy onto the given document;

program code for forming a given relational expression using the input information; and program code for associating the given relational expression with the given document.

37. The computer program product as defined by claim 25 wherein a set of the documents relate to medical studies, the relational expression including at least two of a) inclusion criteria defining a medical condition in a study, b) exclusion criteria defining criteria excluding patients from a study, and c) demographic data of patients in a study.

* * * * *